US009974599B2

(12) United States Patent
Sylvester et al.

(10) Patent No.: US 9,974,599 B2
(45) Date of Patent: May 22, 2018

(54) MULTIPURPOSE ELECTROSURGICAL DEVICE

(71) Applicant: Medtronic PS Medical, Inc., Louisville, CO (US)

(72) Inventors: Joseph Sylvester, Andover, MA (US); Jonathan J. Barry, Rochester, NH (US); Nathan Zamarripa, Kittery Point, ME (US)

(73) Assignee: Medtronic PS Medical, Inc., Louisville, CO (US)

( * ) Notice: Subject to any disclaimer, the term of this patent is extended or adjusted under 35 U.S.C. 154(b) by 402 days.

(21) Appl. No.: 14/808,623

(22) Filed: Jul. 24, 2015

(65) Prior Publication Data

US 2016/0045250 A1    Feb. 18, 2016

Related U.S. Application Data

(60) Provisional application No. 62/037,810, filed on Aug. 15, 2014.

(51) Int. Cl.
*A61B 18/14* (2006.01)
*A61B 18/00* (2006.01)
*A61B 18/12* (2006.01)

(52) U.S. Cl.
CPC . *A61B 18/1402* (2013.01); *A61B 2018/00011* (2013.01); *A61B 2018/00607* (2013.01); *A61B 2018/126* (2013.01); *A61B 2018/1253* (2013.01); *A61B 2018/1412* (2013.01); *A61B 2018/1467* (2013.01); *A61B 2018/1475* (2013.01)

(58) Field of Classification Search
CPC ........ A61B 18/1402; A61B 2018/1253; A61B 2018/126; A61B 2018/1467; A61B 2018/1475; A61B 2018/00178; A61B 2018/00172; A61B 2018/1495; A61B 2018/00916
See application file for complete search history.

(56) References Cited

U.S. PATENT DOCUMENTS

| 2,888,928 A | 6/1959 | Seiger |
| 3,682,130 A | 8/1972 | Jeffers |
| 3,736,936 A | 6/1973 | Basiulis et al. |
| 3,750,650 A | 8/1973 | Ruttgers |

(Continued)

FOREIGN PATENT DOCUMENTS

| DE | 4332898 | 3/1995 |
| WO | 97/40759 | 11/1997 |
| WO | 2011/088387 | 7/2011 |

*Primary Examiner* — Ronald Hupczey, Jr.
*Assistant Examiner* — Tigist Demie
(74) *Attorney, Agent, or Firm* — Jeffrey J. Hohenshell

(57) ABSTRACT

A multipurpose electrosurgical device and methods of use are disclosed. In one example, device includes a handpiece and an end effector having a monopolar electrode and a pair of bipolar electrodes. The end effector is coupled to the handpiece and selectively transitionable relative to the handpiece from a first position to a second position. The first position includes the bipolar electrodes extending distally from the device and the monopolar electrode is spaced from a distal end portion of the device. The second position includes the monopolar electrode extending distally and the bipolar electrodes are spaced from a distal end portion of the device.

28 Claims, 12 Drawing Sheets

(56) References Cited

U.S. PATENT DOCUMENTS

| | | |
|---|---|---|
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,060,088 A | 11/1977 | Morrison, Jr. et al. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scorochenko |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,936,281 A | 6/1990 | Stasz |
| 4,943,290 A | 7/1990 | Rexroth et al. |
| 4,946,460 A | 8/1990 | Merry et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,190,541 A | 3/1993 | Abele et al. |
| 5,195,959 A | 3/1993 | Smith |
| 5,197,964 A | 3/1993 | Parins |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,234,428 A | 8/1993 | Kaufman |
| 5,254,116 A | 10/1993 | Baust et al. |
| 5,254,117 A | 10/1993 | Rigby et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |

(56) References Cited

U.S. PATENT DOCUMENTS

| | | |
|---|---|---|
| 5,560,362 A | 10/1996 | Silwa, Jr. et al. |
| 5,562,702 A | 10/1996 | Huitema et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,637,090 A | 9/1997 | McGee et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,928,191 A | 9/1999 | Houser et al. |
| 5,954,661 A | 9/1999 | Greenspon et al. |
| 5,971,980 A | 10/1999 | Sherman |
| 5,971,983 A | 10/1999 | Lesh |
| 5,975,919 A | 11/1999 | Arnett et al. |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble et al. |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |

(56) References Cited

U.S. PATENT DOCUMENTS

| | | |
|---|---|---|
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,217,528 B1 | 4/2001 | Koblish et al. |
| 6,217,575 B1 | 4/2001 | DeVore |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | McClurken et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,115,139 B2 | 10/2006 | McClurken et al. |
| 7,156,845 B2 | 1/2007 | Mulier et al. |
| 7,232,440 B2 * | 6/2007 | Dumbauld ......... A61B 18/1445 606/45 |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |

(56) References Cited

U.S. PATENT DOCUMENTS

| | | |
|---|---|---|
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | McClurken et al. |
| 7,645,277 B2 | 1/2010 | McClurken et al. |
| 7,651,494 B2 | 1/2010 | McClurken et al. |
| 7,736,361 B2 | 6/2010 | Palanker |
| 7,811,282 B2 | 10/2010 | McClurken |
| 7,815,634 B2 | 10/2010 | McClurken et al. |
| 7,909,820 B2 | 3/2011 | Lipson |
| 7,976,544 B2 | 7/2011 | McClurken |
| 7,998,140 B2 | 8/2011 | McClurken |
| 8,012,154 B2 | 9/2011 | Livneh |
| 8,038,670 B2 | 10/2011 | McClurken |
| 8,048,070 B2 | 11/2011 | O'Brien |
| 8,083,736 B2 | 12/2011 | McClurken et al. |
| 8,177,783 B2 | 5/2012 | Davison et al. |
| 8,216,233 B2 | 7/2012 | McClurken |
| 8,323,276 B2 | 12/2012 | Palanker et al. |
| 8,348,946 B2 | 1/2013 | McClurken |
| 8,906,012 B2 | 12/2014 | Conley et al. |
| 8,920,417 B2 | 12/2014 | Conley et al. |
| 2002/0049483 A1 | 4/2002 | Knowlton |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |
| 2006/0064085 A1 | 3/2006 | Schechter et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2009/0264879 A1 | 10/2009 | McClurken et al. |
| 2010/0100095 A1 | 4/2010 | McClurken et al. |
| 2011/0028965 A1 | 2/2011 | McClurken |
| 2012/0004657 A1 | 1/2012 | Conley et al. |
| 2012/0101496 A1 | 4/2012 | McClurken et al. |
| 2012/0116397 A1 | 5/2012 | Rencher et al. |
| 2012/0191084 A1 | 7/2012 | Davison et al. |
| 2014/0276804 A1* | 9/2014 | Batchelor .......... A61B 18/1442 606/45 |
| 2015/0080879 A1* | 3/2015 | Trees .................. A61B 18/1445 606/40 |

* cited by examiner

MULTIPURPOSE ELECTROSURGICAL DEVICE

This Non-Provisional Patent Application claims the benefit of U.S. Provisional Patent Application Ser. No. 62/037,810, filed Aug. 15, 2014, and titled "MULTIPURPOSE ELECTROSURGICAL DEVICE," which is herein incorporated by reference to the extent it is not inconsistent with this disclosure.

BACKGROUND

This disclosure relates generally to the field of medical devices, systems and methods for use in surgical procedures. More specifically, this disclosure relates to electrosurgical devices, systems and methods that provide for cutting, coagulation, hemostasis and sealing of bodily tissues with a single electrosurgical device.

Historically, two distinct electrosurgical devices, one monopolar and the other bipolar, were use to perform different functions in surgery, such as tissue cutting and tissue sealing. For example a surgeon would use a monopolar electrosurgical device to cut tissue and use a bipolar electrosurgical device to seal the tissue. When these different functions were performed during a surgical procedure, surgeons would switch between different devices. Switching between devices can lead to undesirable effects such as longer procedure times, higher costs, and an increased likelihood of inaccuracy or imprecision.

To address these issues, some electrosurgical devices capable of performing both cutting and sealing of tissue, including fluid-assisted sealing of tissue, have been developed. Several such electrosurgical device are described, for example, in U.S. Pat. No. 8,632,533 to Greeley, et al., U.S. Patent Application Publication No. 2012/000465 to Conley, et al., U.S. Patent Application Publication No. 2011/0178515 to Bloom et al., each assigned to the assignee of the present disclosure and incorporated by reference herein in their entireties to the extent they are not inconsistent with the present disclosure.

Several devices that have been developed include a hand piece having two electrodes. These devices can be configured as bipolar electrodes connected to a source of bipolar power to operate in a bipolar mode, for example to seal tissue. To operate the same two-electrode device in a monopolar mode, for example to cut tissue, one of the two electrodes may be selectively deactivated and the other of the two electrodes coupled to a source of monopolar power. During monopolar operation, the monopolar electrode of the device may be used in conjunction with a ground pad dispersive electrode placed on a patient, which is commonly known as a patient return electrode or grounding pad. In this manner, the dual function device may provide treatment to tissue utilizing one or both electrodes depending upon the desired tissue treatment.

Despite having the ability to perform different functions with a single device, when monopolar function is desired only one of the two electrodes of the device are utilized and the deactivated second electrode may obstruct the view of the surgeon during the monopolar operation. Furthermore, the deactivated electrode may unnecessarily prevent the monopolar electrode from entering smaller spaces or tissue areas that could otherwise be accessed if the unused electrode was not exposed. In devices where the problem of an obstructive deactivated second electrode has been addressed, may not provide for a robust electrode/tissue interface when the device is used in bipolar mode. Further still, devices may not perform similarly to independent bipolar and monopolar devices.

SUMMARY

This summary is provided to introduce a selection of concepts in a simplified form that are further described below in the Detailed Description. This summary is not intended to identify key features or essential features of the claimed subject matter, nor is it intended to limit the scope of the claimed subject matter.

A multipurpose electrosurgical device and methods of use are disclosed. In one example, the device includes a handpiece and an end effector rotatably coupled to the handpiece. In one particular example, the handpiece includes distally extending first and second arms, and the end effector is rotatably coupled to the first and second arms. The end effector includes monopolar and bipolar electrode ends. Rotation of the end effector with respect to the handpiece allows the device to be selectively configurable for use in a bipolar and a monopolar mode. In one example, the device includes a fluid delivery path and electrical connection of the monopolar and bipolar electrode ends to a source of electrical energy that allows the end effector to rotate freely with respect to the handpiece.

In one aspect, the disclosure relates to a multipurpose electrosurgical device. The multipurpose surgical device in this aspect includes a handle and first and second arms extending distally from the handle. The first and second arms are laterally spaced from each other to provide a gap between the first and second arms. An end effector is rotatably coupled to the first and second arms in the gap. The end effector includes bipolar and monopolar electrode ends. In one particular example, the end effector includes axially opposed electrode ends. The end effector is configured to rotate such that the bipolar and monopolar electrode ends are rotatable with respect to the first and second arms to selectively configure the device in a bipolar mode and a monopolar mode.

In another aspect, the disclosure relates to a multipurpose electrosurgical device. The multipurpose electrosurgical device in this aspect includes a handpiece and an end effector having a monopolar electrode and a pair of bipolar electrodes. The end effector is coupled to the handpiece and selectively transitionable relative to the handpiece from a first position to a second position. The first position includes the bipolar electrodes extending distally from the device and the monopolar electrode is spaced from a distal end portion of the device. The second position includes the monopolar electrode extending distally and the bipolar electrodes are spaced from a distal end portion of the device. In one particular example, the first position includes the monopolar electrode disposed within the handpiece and the second position includes the bipolar electrodes disposed within the handpiece.

In still another aspect, the disclosure relates to a method of selectively configuring an electrosurgical device for use in a bipolar mode and a monopolar mode. The method includes configuring the device in a bipolar mode by rotating an end effector rotatably coupled to first and second arms extending distally from a handle of the device to position a bipolar end of the end effector such that the bipolar end extends distally from the handle and a monopolar end of the end effector is at least partially received within an open space between the first and second arms. The method also includes configuring the device in a monopolar mode by rotating the end effector to position the monopolar end of the end effector such that the monopolar end extends distally from the handle and the bipolar end is at least partially received within the open space. Rotating the end effector includes rotating the end effector by hand.

DETAILED DESCRIPTION

Figure 1:
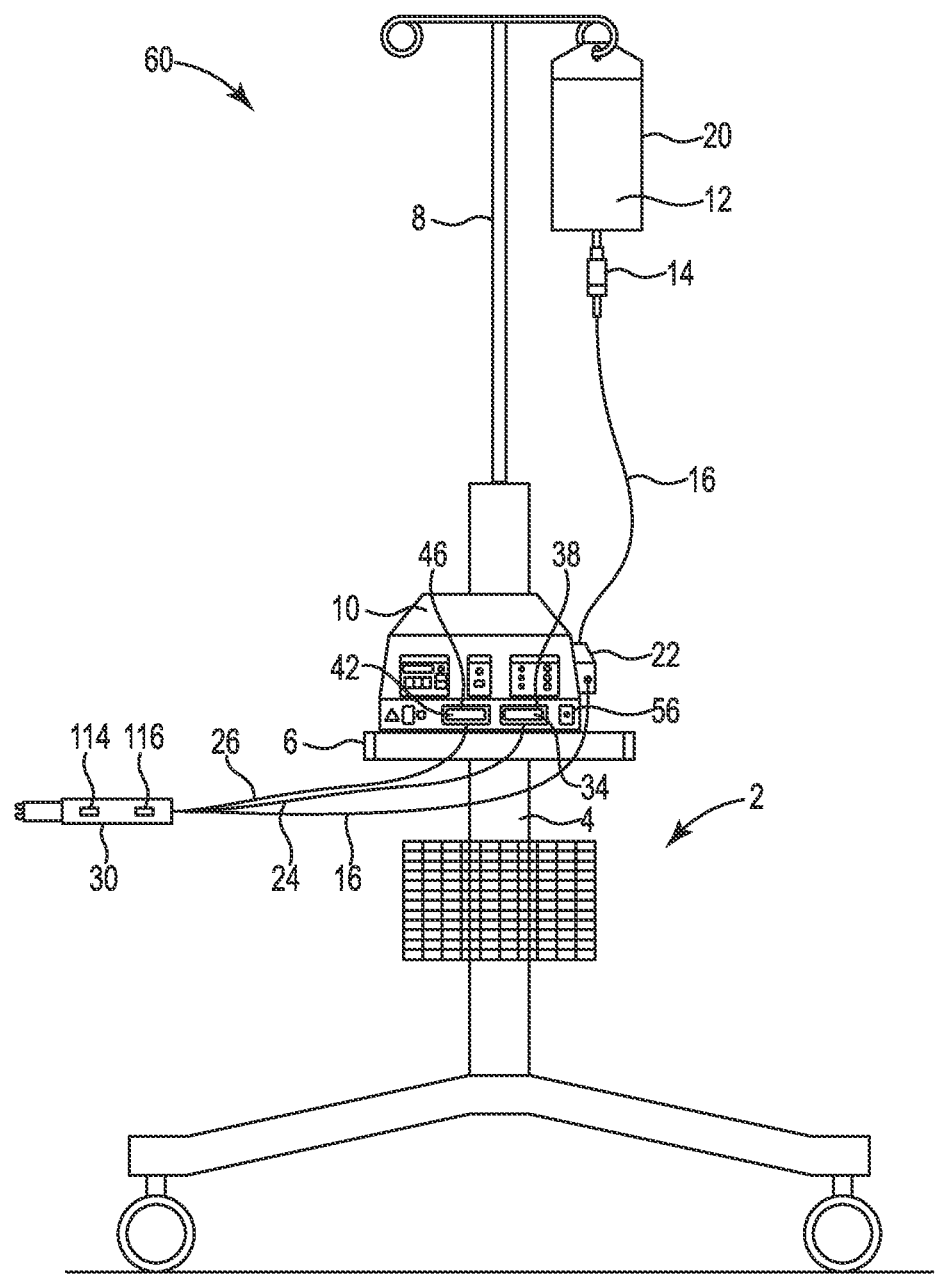
FIG. 1 is a front view of an embodiment of a system according to the present disclosure including an example electrosurgical unit in combination with a fluid source and handheld electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a front view of one example of a system 60 that includes an electrosurgical unit 10 in combination with a fluid source 20 and an example handheld electrosurgical device 30. The device 30 can be a multipurpose device configurable for use in cutting and sealing, including electrocautery and coagulation, of tissue and configurable for use in both a monopolar and a bipolar mode.

The system 60 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 is configured to provide both monopolar and bipolar radio-frequency (RF) power output. Electrosurgical unit 10 can include a lock out feature preventing both monopolar and bipolar output from being simultaneously activated. Alternatively, device 30 can be simultaneously coupled to two separate electrosurgical units such as a first unit to supply device 30 with monopolar power and a second unit to supply device 30 with bipolar power.

During monopolar operation of electrosurgical device 30, a first electrode, often referred to as the active electrode, is provided with electrosurgical device 30 while a second electrode (not shown), often referred to as the indifferent or neutral electrode, is provided in the form of a ground pad dispersive electrode located on a patient. For example, the ground pad dispersive electrode is typically on the back, buttocks, upper leg, or other suitable anatomical location during surgery. In such a configuration, the ground pad dispersive electrode is often referred to as a patient return electrode. An electrical circuit of RF energy is formed between the active electrode and the ground pad dispersive electrode through the patient.

During bipolar operation of electrosurgical device 30, a second electrode providing a second electrical pole is provided as part of the device 30. The ground pad dispersive electrode is not used. An electrical circuit of RF energy is created between the first and second poles of the device 30. The current no longer flows through the patient's body to the ground pad dispersive electrode, but rather through a localized portion of tissue between the poles of the device 30.

The electrosurgical device 30 in the example is connected to electrosurgical unit 10 via cables 24 and 26. Cable 24, with plug 34, connects to bipolar output receptacle 38 while cable 26, with plug 42, connects to monopolar output receptacle 46 of electrosurgical unit 10. When electrosurgical unit 10 may be used in monopolar mode, an additional cable may connect a ground pad electrode to a ground pad receptacle of the electrosurgical unit 10. In some examples, delivery tubing 16 and cables 24, 26 are combined to form a single cable.

Figure 2:
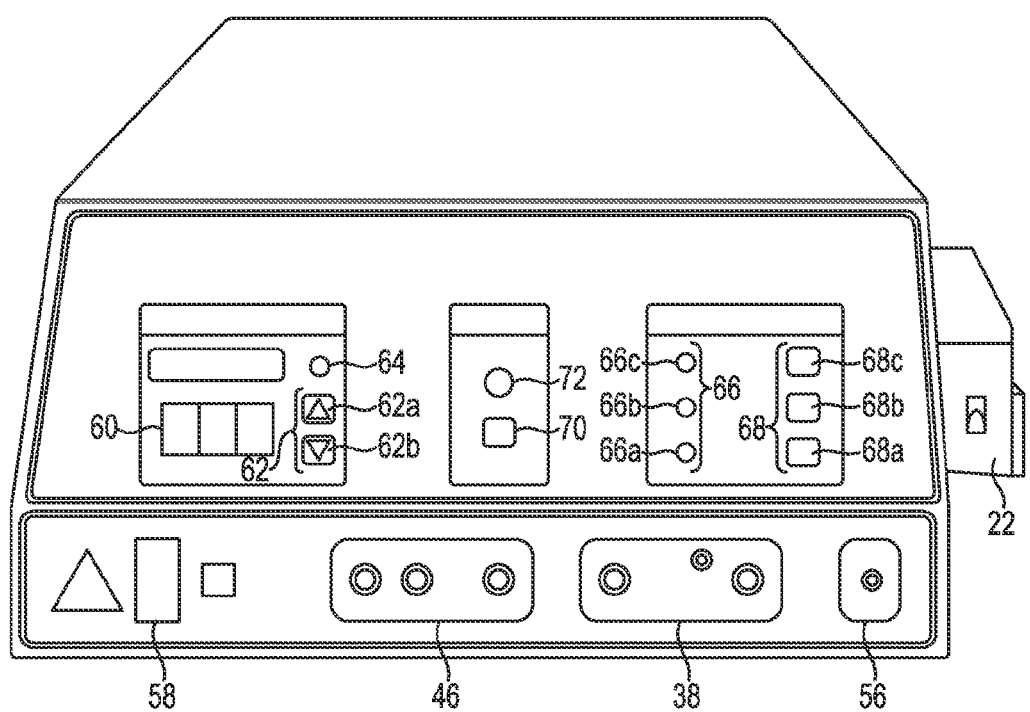
FIG. 2 is front perspective view of the electrosurgical unit of FIG. 1.

FIG. 2 illustrates a front panel of an example electrosurgical unit 10. The features of electrosurgical unit 10 described are for illustration, and the electrosurgical units suitable for use with device 30 may include some, all, or other features than those described below.

The electrical surgical unit 10 includes a power switch 58 to turn the unit on and off and an RF power setting display 60 to display the RF power supplied to the electrosurgical device 30. The power setting display 60 can display the RF power setting numerically in a selected unit such as watts.

The example electrosurgical unit 10 includes an RF power selector 62 comprising RF power setting switches 62a, 62b that are used to select or adjust the RF power setting. A user can push switch 62a to increase the RF power setting and push switch 62b to decrease the RF power setting. In the example, switches 62a, 62b are membrane switches. In another example, the electrosurgical unit may include more than one power selectors such as a power selector for monopolar power selection and a power selector for bipolar power selection. The electrosurgical unit can also include an RF power activation display 64 having an indicator light that can illuminate when the RF power is activated either via a hand switch on the device 30, a foot switch, or other switch.

The example electrosurgical unit 10 also includes fluid flow rate setting display 66 and flow rate setting selector 68. The display 66 includes indicator lights 66a, 66b, 66c, and selector 68 includes switches 68a, 68b, 68c. In the example, switches 68a, 68b, 68c are membrane switches. Pushing one of the switches 68a, 68b, 68c selects a fluid flow rate, which is than indicated in display 66. Indicator light 66a corresponds with a fluid flow rate setting of low, which can be provided by pushing switch 68a. Indicator light 66b corresponds with a fluid flow rate setting of medium, which can be provided by pushing switch 68b. Indicator light corresponds with a fluid flow rate setting of high, which can be provided by pushing switch 68c.

Device 30 can be primed with fluid 12 prior to beginning a surgical procedure. Priming may be desirable to inhibit activating the RF power without the presence of fluid 12. The example electrosurgical device 10 can also include a priming switch 70 to initiate priming of the device 30. In one example, the depressing the priming switch will operate the pump for a predetermined amount of time or fluid flow to prime the device 30. After the device 30 has been primed, the pump 22 may shut off automatically. The electrosurgical unit 10 can include a priming display 72 that illuminates an indicator light while the device 30 is priming.

Figure 3:
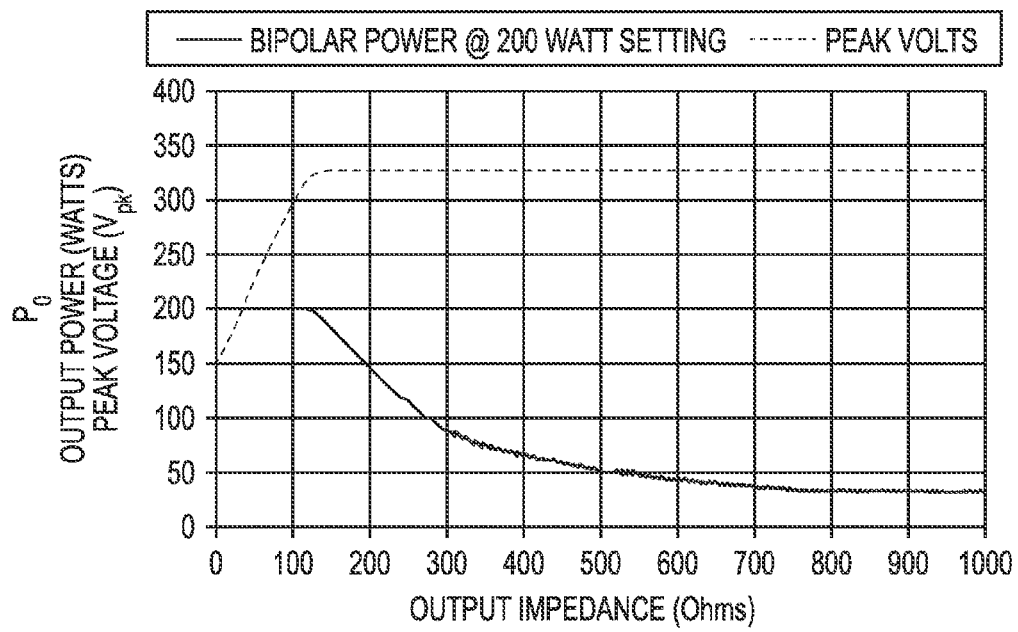
FIG. 3 is a graph of a bipolar radio frequency power output versus impedance for the electrosurgical unit of FIG. 1.

FIG. 3 illustrates an example bipolar RF power output versus impedance for the electrosurgical device 10. Impedance Z is indicated in units of ohms on the X-axis and output power $P_O$ is indicated in units of watts on the Y-axis. The bipolar power (RF) setting $P_S$ for the electrosurgical device 10 is selected at 200 watts in the example. As illustrated, the power output $P_O$ for the selected power setting $P_S$ generally remains constant for an impedance Z between the low impedance cut-off of 30 ohms and the high impedance cut-off of 120 ohms. Below an impedance Z of 30 ohms, the output power $P_O$ for the selected power setting $P_S$ will decrease; and above an impedance Z of 120 ohms, the output power $P_O$ for the selected power setting $P_S$ will increase.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Figure 4:
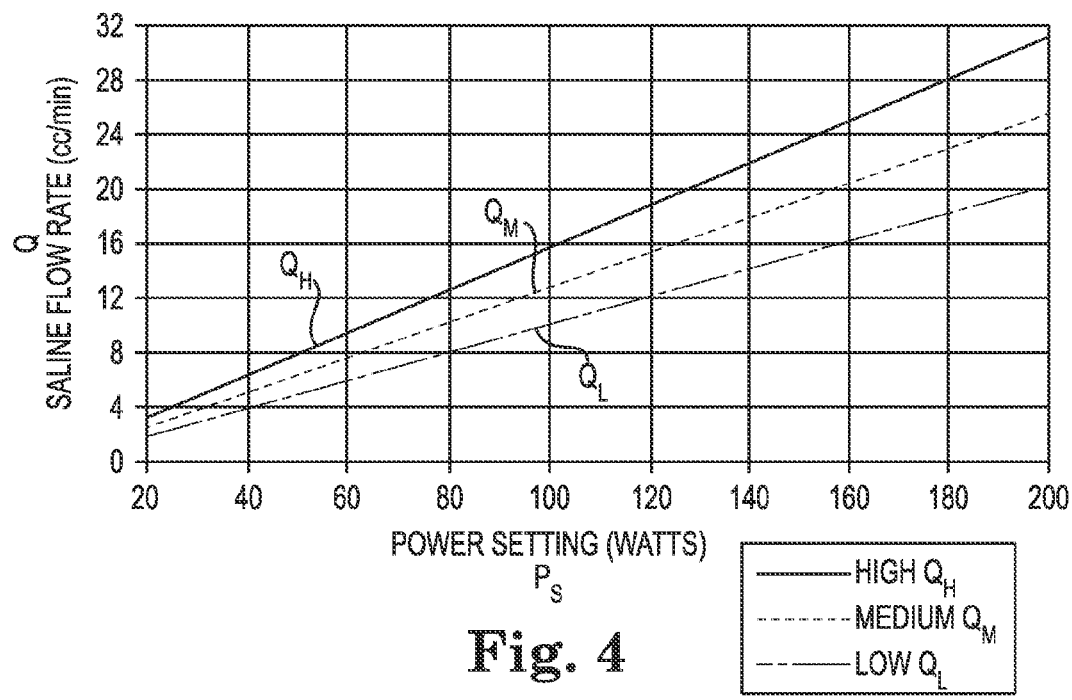
FIG. 4 is a graph of illustrating a relationship of radio frequency power setting to fluid flow rate.

FIG. 4 illustrates an example functional relationship of fluid flow rate Q in units of cubic centimeters per minute (cc/min) on the Y-axis and RF power setting $P_S$ in units of watts on the X-axis. While not being bound to a particular theory, the relationship between the variables can be configured to inhibit undesired effects such as tissue desiccation, electrode sticking, smoke production, char formation, and other effects while not providing a fluid flow rate Q at a corresponding RF power setting $P_S$ not so great as to disperse too much electricity and or overly cool the tissue at the electrode/tissue interface. Electrosurgical unit 10 is configured to increase the fluid flow rate Q generally linearly with an increasing RF power setting $P_S$ for each of the three fluid flow rate settings of low, medium, and high corresponding to $Q_1$, $Q_2$, $Q_3$, respectively.

In examples of system 60 that do not include a pump for fluid 12, there may not be a preset functional relationship between fluid flow rate Q and RF power setting $P_S$ stored in electrosurgical unit 10. Rather than the fluid flow rate Q being automatically controlled by the electrosurgical unit 10 based on RF power setting $P_S$, the fluid flow rate Q may be manually controlled, such as by the user of the device 30 or another clinician with a roller or pinch clamp or other clamp provided with system 60 and configured to act upon and compress the tubing 16 to control flow.

While multipurpose electrosurgical surgical device 30 is described with reference to electrosurgical unit 10 and other elements of system 60, it should understood the description of the combination is for the purposes of illustrating system 60. It may be possible to use the multipurpose electrosurgical device 30 in other systems or the electrosurgical unit 10 may be used with other electrosurgical devices.

Figure 5:
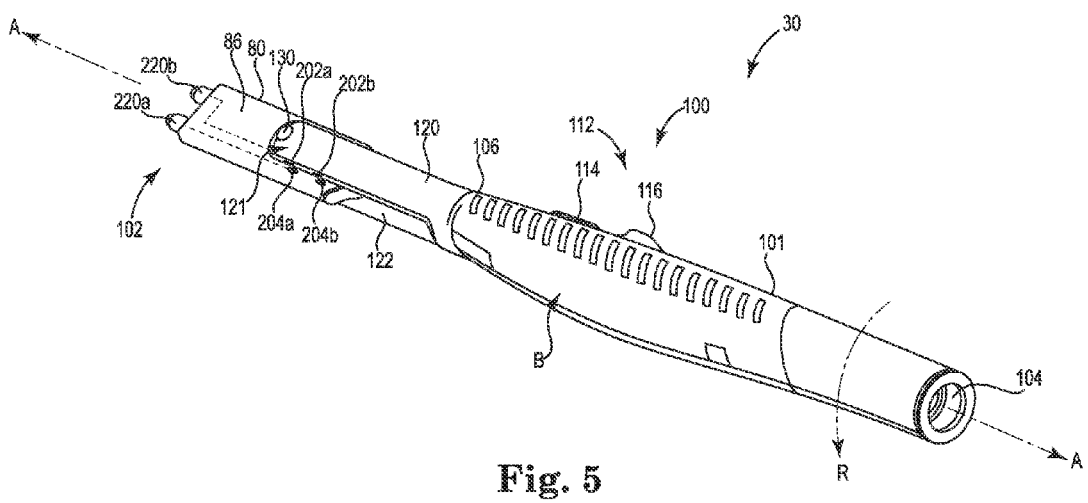
FIG. 5 is a perspective view of the example handheld electrosurgical device of FIG. 1 configured for use in a bipolar mode.
Figure 6:
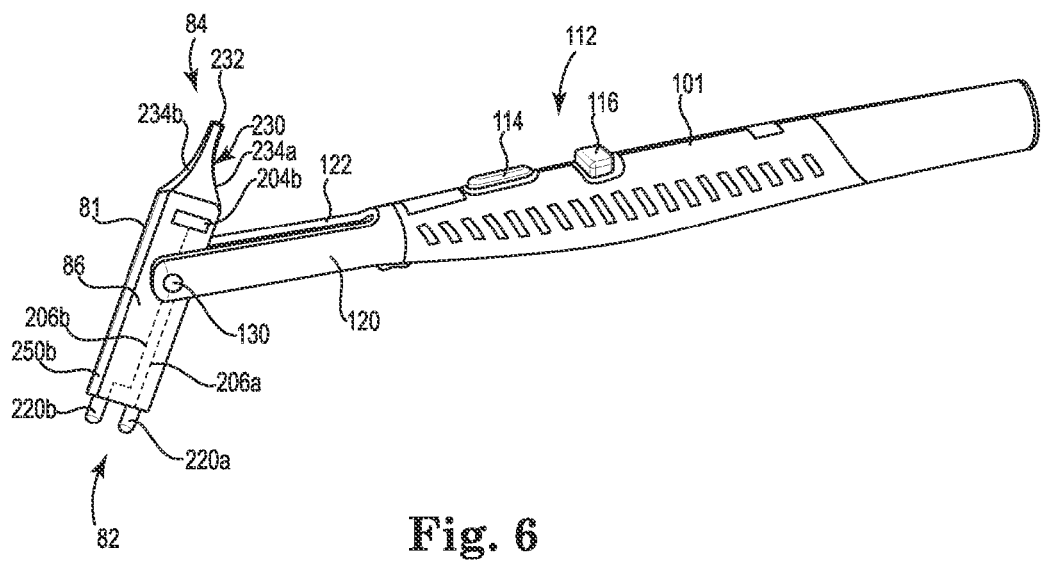
FIG. 6 is a perspective view of the electrosurgical device of FIG. 5 during rotation of an end effector.
Figure 7:
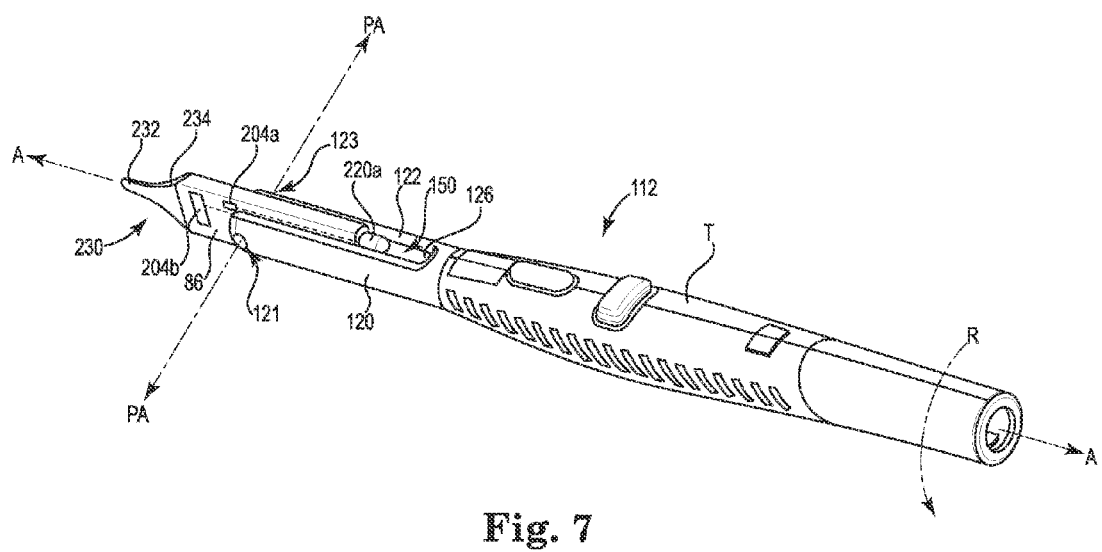
FIG. 7 is a perspective view of an embodiment of the handheld electrosurgical device of FIG. 5 configured for use in a monopolar mode.

FIGS. 5-7 illustrate an exemplary multipurpose electrosurgical device 30 constructed in accordance with the disclosure. As a point of reference, FIGS. 6 and 7 show the device 30 rotated about a longitudinal axis A in the direction R as compared to the position of device 30 in FIG. 5.

The device 30 includes a handpiece 100 having a handle 101 and one or more arms extending distally from the handle 101. The example illustrates a pair of arms 120, 122 extending distally from the handle 101 and laterally spaced from each other to provide a gap 150 between the arms 120, 122. An end effector 80 is rotatably coupled to the arms 120, 122 and partially disposed in the gap 150. The end effector 80 includes bipolar and monopolar electrode ends 82, 84, respectively. A user can selectively rotate the end effector 80 with respect to the arms 120, 122 about axis PA from a first position, as shown in FIG. 5, in which the device 30 is configured to operate in bipolar mode—through mid-rotation or partial rotation as shown in FIG. 6.—to a second position, as shown in FIG. 7, in which the device 30 is configured to operate in monopolar mode. A user may rotate the end effector by hand.

The device 30 includes three electrode tips that can be used to selectively treat tissue. Two electrodes tips 220a, 220b extend distally from the device and are used in bipolar mode when the device 30 is configured in the first position. Electrode blade 230 extends distally from the device and is used in monopolar mode when the device is configured in the second position. While in the first position, the electrode blade 230 is spaced from a distal end portion of the device. For example, the electrode blade 230 does not extend distally form the device and can be tucked away within the arms 120, 122 of the handpiece 100. The electrode tips 220*a*, 220*b* are spaced from the distal end portion of the device and can be tucked away within the arms 120, 122 of the handpiece 100 while the device is configured in the second position. Device 30 has the ability to perform different functions while reducing or eliminating the adverse issues of previous multipurpose electrosurgical devices. With device 30, electrodes used in bipolar mode, such as electrodes tips 220*a*, 220*b*, do not obstruct view or unnecessarily prevent the monopolar electrode blade 230 from entering smaller spaces or tissue areas. Further, the co-planar arrangement of the electrode tips 220*a*, 220*b* multipurpose device 30 provides for a robust electrode/tissue interface in bipolar mode.

Device 30 includes an elongated handpiece 100 with handle 101, a distal end portion 102 and a proximal end 104. In the example, delivery tubing 16 for providing fluid 12 to the device 30 and cables 24, 26 for providing bipolar and monopolar energy, respectively, to the device can be coupled to the proximal end 104. Handpiece 100 may be configured to enable a user of device 30 to hold and manipulate device 30 between the thumb and index finger like a writing instrument. Handle 101 may comprise a sterilizable, rigid, electrically insulative material, such as a synthetic polymer (e.g., polycarbonate, acrylonitrile-butadiene-styrene). The handle 101 can include a lower surface, or bottom B, which is better illustrated in FIG. 5, and an upper surface, or top T, which is better illustrated in FIGS. 6 and 7.

The handpiece 100 includes a switch mechanism 112 to complete an electrical circuit between a conductor on the proximal end 104 and the end effector 80. In one example, the switch mechanism 112 includes push buttons 114 and 116 projecting from the upper surface or top T of the handle 101. Push buttons 114, 116 comprise hand switch assemblies for forming a closed circuit that can be sensed by an electrosurgical unit, such as electrosurgical unit 10 of FIG. 2, to selectively provide monopolar or bipolar power, respectively. In another example, switch mechanism 112 includes a single push button switch on the handpiece 100 to deliver both bipolar power and monopolar power depending on whether the device 30 is configured in the first position or the second position, respectively.

Two elongated, rigid, electrically insulative shafts formed as arms 120, 122 extend from handle 101. Arms 120, 122 can be paddle-shaped or comprise a cylindrical outer surface that, in the example, matches a curvature of the handle 101. Further, arms 120, 122 can comprise outer dimensions that are mirror images of one another. Arms 120, 122 are separated by an empty space or gap 150 and form a U-shaped or clevis-shaped member. In this way, arms 120, 122 may be referred to as clevis arms 120, 122. For reference, arm 120 may be considered a first clevis arm or first arm and arm 122 may be considered a second clevis arm or second arm.

End effector 80 comprises a body 81 having first and second ends, 82, 84, and laterally opposed first and second lateral surfaces or sides 86, 88 joined by lateral edges 250*a*, 250*b* that may comprise rounded or chamfered edges configured so as to minimize or avoid inadvertent damage to tissue. Sides 86, 88 of end effector 80 may comprise substantially flat or planar surfaces. First end 82 may comprise an electrode working end comprising a bipolar electrode end 82, or bipolar end 82. Second end 84 may comprise an electrode working end comprising a monopolar electrode end 84, or monopolar end 84. In the illustrated example, the first and second ends 82, 84 are axially opposed. Other configurations are possible. For example, an end effector may be configured to be L-shaped, where ends 82, 84 are not axially opposed. Instead, the end effector can be configured such that when one end distally extends from the device 30, the other end is spaced from the distal end of the device.

The elongated end effector 80 is rotatably coupled to first and second arms 120, 122 via a pivot or hinge such as a clevis pin 130 coupled to distal end portions 121, 123 of each of arms 120, 122. In the example, clevis pin 130 extends through a portion of end effector 80 to couple end effector 80 to arms 120, 122. Although the example shows pin 130 centrally located along end effector body 81, the pin 130 may be placed at various locations along body 81. In one example, the clevis pin 130 is fixed relative to movement with the arms 120, 122, and the end effector 80 rotates about axis PA relative to the clevis pin 130 and arms 120, 122. In another example, the end effector is 80 is fixed relative to movement with the clevis pin 130, and the end effector 80 and clevis pin 130 rotate about axis PA relative to the arms 120, 122. Other examples are contemplated.

The end effector 80 is rotated about pivot or pin 130 to position at least a portion of one of the bipolar end 82 or monopolar end 84 between arms 120 and 122 and the other of the bipolar end 82 and monopolar end 84 to project distally from arms 120, 122. FIG. 5 shows monopolar end 84 between arms 120, 122 and the bipolar end projecting distally from arms 120, 122. A user can adjust the position of the end effector by hand. FIG. 6 depicts end effector 80 in partial-rotation about axis PA of pin 130 as the end effector 80 is spun about pin 130 to change from the bipolar or coagulation mode of FIG. 5 to a monopolar or cut mode as illustrated in FIG. 7. FIG. 7 depicts the end effector 80 after 180 degree rotation of end effector 80 about pin 130 from the position shown in FIG. 5. In this configuration, the device 30 is configured for use in a monopolar or cut mode.

Pin 130 may comprise a locking mechanism or a quick-release mechanism enabling efficient change out from one mode to another or enabling effective locking into place of the end effector 80 once the desired end 82 or 84 is in place projecting distally from arms 120, 122. In another example, a locking mechanism may be placed elsewhere on one or both of arms 120, 122 to connect with end effector 80 to yieldably hold and release the end effector in place when configured in the first position, the second position, or both. In another example, the arms 120, 122 may be offset from the handle 101 by 90 degrees from the configuration shown in the figures, in the direction R or in the opposite direction on axis A to help hold the end effector 80 in place. This helps maintain the position of the end effector 80 with respect to the arms 120, 122 during surgery because pressure is not placed in a way to rotate the end effector 80 with respect to the arms 120, 122.

In the example, end effector 80 can rotate 360 degrees or freely about axis PA of the pin 130 with respect to arms 120, 122. For example, the end effector 80 can be rotated between the first position and the second position over and over again in the same direction of rotation or in the opposite direction. In the example, axis PA is generally perpendicular to handle axis A. Alternatively, rotation of the end effector 80 can be limited, such as limited to 180 degrees to transition between the first position to the second position in first direction of rotation and return to the first position in an opposite direction of rotation. In examples where rotation of the end effector 80 is limited, the device 30 can include a tang coupled to arms 120, 122 via the clevis pin 130.

Figure 8:
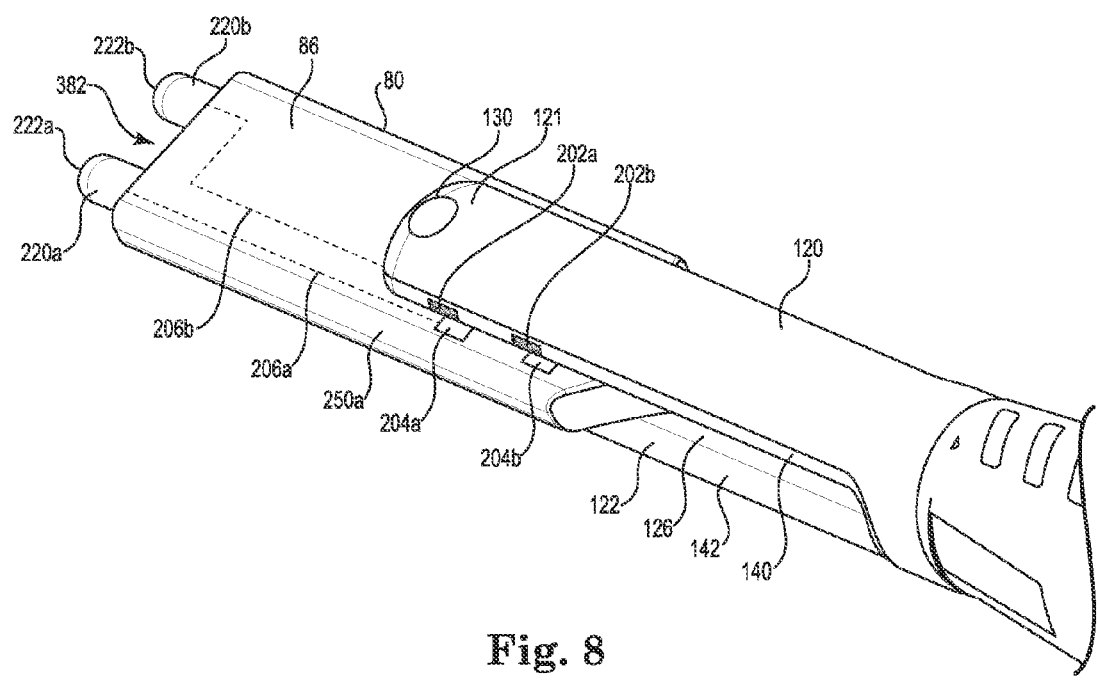
FIG. 8 is a close-up perspective view of a distal end portion of the electrosurgical device as configured in FIG. 5 for use in a bipolar mode.
Figure 10:
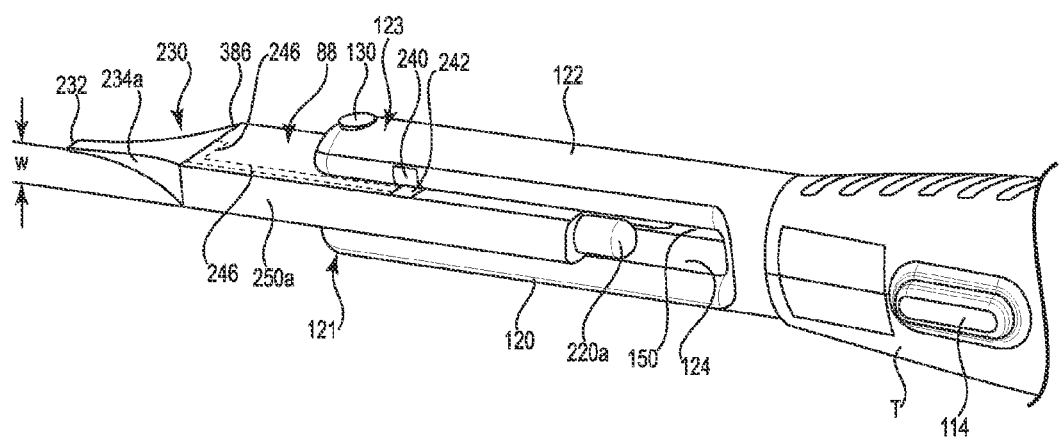
FIG. 10 is a close-up perspective view of a distal end portion of the electrosurgical device as configured of FIG. 7 for use in a monopolar mode.

FIGS. 8 and 10 illustrate additional details of the multi-purpose electrosurgical device 30. FIG. 8 illustrates a close-up view of the distal end portion 102 of multipurpose electrosurgical device 30 configured in the first position, or bipolar mode, as shown in FIG. 5. FIG. 10 illustrates a close-up view of the distal end portion 102 of multipurpose electrosurgical device 30 configured in the second position, or monopolar mode, as shown in FIG. 7. As a point of reference, FIG. 10 shows device 30 rotated about the longitudinal axis A in the direction R as compared to the position of the device 30 in FIG. 7.

Arms 120, 122 may be formed as substantially flat or paddle-shaped arms and comprise opposed inner 124, 126 and outer 125, 127 surfaces joined by lateral edges 140, 142, respectively. In the example, first and second arm inner surfaces 124, 126 are substantially flat while first and second arm outer surfaces 125, 127 are slightly convex or rounded, while maintaining a low profile. Alternatively, surfaces 125, 127 may likewise include generally planar or flat surfaces. Example lateral edges 140, 142 include rounded or chamfered edges configured to minimize or avoid damage to tissue.

The spacing or gap 150 between clevis arms 120, 122 is configured such that an end 82, 84 of the end effector 80 may be received between the arms 120, 122. Selective rotation of the end effector 80 about the pin 130 causes one or the other of first and second ends 82, 84 to be received within the space 150 between clevis arms 120 and 122. The size of the space 150 can be based upon the size, or more specifically, the width W of the end effector 80. For example, the spacing or gap 150 between arms 120 and 122 can be sized so as to allow or provide friction contact of first and second end effector sides 86, 88 with first and second clevis arm inner surfaces 124, 126, respectively. In another example, the gap 150 can be sized to allow for minimal or no contact between the end effector sides 86, 88 and clevis arm inner surfaces 124, 126, respectively.

In FIG. 8, the device 30 is configured such that the end effector first, bipolar end 82 is projecting distally from the arms 120, 122 while the end effector second, monopolar end 84, partially obstructed from view by arm 120, is received in gap or spacing 150 as described above. Bipolar end 82 comprises two electrode tips 220a, 220b for treating tissue. Electrode tips 220a, 220b extend from end effector body 81 and, in the example, include blunt, rounded tips having distal-most electrode ends 222a, 222b, respectively. "Distal-most" for electrode tips 220a, 220b refers bipolar end 82. Distal-most electrode ends 222a, 222b may provide smooth continuous surfaces and in one example are devoid of points or edges. Electrode tips 220a, 220b may be configured to optimize tissue sealing or coagulation in conjunction with delivery of fluid or for a particular application or anatomical geometry.

Electrode tips 220a, 220b are configured to be electrically coupled to a source of bipolar RF energy supplied from an electrosurgical unit, such as electrosurgical unit 10. Device to further includes bipolar contact points 202a, 202b disposed on the one or both of clevis arms, such as on arm 120. Contact points 202a, 202b are configured to mate with contact points 204a, 204b, respectively, disposed on end effector 80, when the device is configured in the first position to operate in bipolar mode. When contact points 202a, 202b mate with contact points 204a, 204b on the end effector 80, the device 10 is configured to transfer electrical energy from the switch on the handpiece 100, such as pushbutton 116, to the electrode tips 220a, 220b. In one example, RF energy from an electrical surgical unit can be transferred through mated points 202a, 204a and 202b, 204b to electrode tips 220a, 220b, respectively. In another example, mated points can be used to complete a connection between other conductors used to transfer RF energy from the electrosurgical unit and the electrode tips 220a, 220b.

Figure 9:
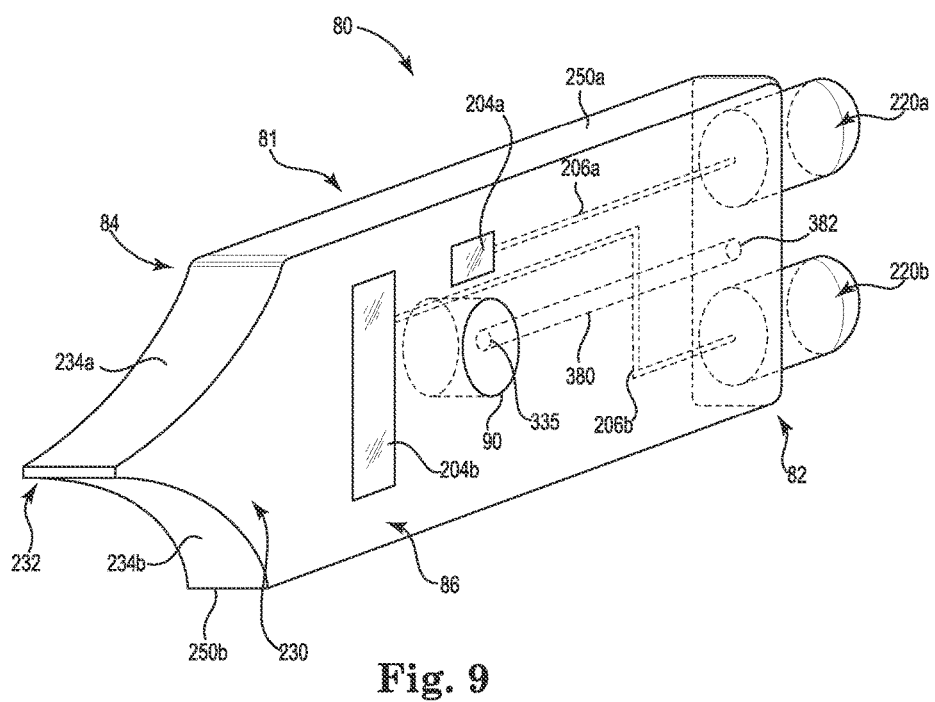
FIG. 9 is a close-up perspective view of the end effector of the electrosurgical device of FIG. 5 showing inner structures in phantom.

FIG. 9 illustrates a perspective view of end effector 80 decoupled from the clevis pin 130 and handpiece 100 with inner structures shown in phantom. In the example shown, end effector 80 includes an opening 90 extending through the body 81 from sides 86, 88 configured to receive clevis pin 130. Electrode tips 220a, 220b comprise an electrically conductive material such as metal and may comprise stainless steel, titanium, gold, silver, platinum or any other suitable material. Tips 220a, 220b are electrically coupled to first and second electrically conductive bipolar electrode paths 206a, 206b respectively. Conductive bipolar electrode paths 206a, 206b may comprise an electrically conductive material and may be configured as a wire or wire trace, or other conductor, within the end effector body 81 or on the surface of the end effector body 81. In some examples, the paths 206a, 206b may be covered with an insulator material if disposed on the surface of the end effector body 81. Conductive bipolar electrode paths 206a, 206b extend proximally from electrode tips 220a, 220b to a pair of electrically conductive bipolar electrode contact points 204a, 204b, respectively, that may be provided on the first side or surface 86 of end effector 80 in a position to mate with points 202a, 202b.

In one example, points 202a, 202b and pads 204a, 204b, are electrically conductive generally pads. In such an example, bipolar electrode contact pads 204a, 204b are configured to frictionally contact first and second electrically conductive mating bipolar pads 202a, 202b provided on a surface of an arm, such as the first arm 120 in the example, of the device 30. When the bipolar electrode points 204a, 204b make contact with mating bipolar points 202a, 202b on arm 120, bipolar energy may be delivered from an electrosurgical unit 10 via depression of push button 116. Energy from the unit 10 may be delivered via electrically conductive, insulated shafts within the handle 101 and arm 120. An electrically conductive path may thus be established from the proximal end 104 of handle 101, through first arm 120 and to mating bipolar points 202a, 202b, 204a, 204b. In this manner, bipolar electrical energy may be delivered to tissue via bipolar electrode tips 220a, 220b. When the device 30 is configured as shown in FIG. 8, the device 30 may be considered to be in a bipolar, tissue sealing, coagulation or electrocautery mode.

Points 202a, 202b and points 204a, 204b may take other suitable forms. For example, points 202a, 202b may be pads formed as concave dimples or generally flat surfaces designed to mate with points 204a, 204b that are pads formed as concave bumps, or vice versa. The dimple and bump design may also provide a tactile sensation indicating the end effector 80 is in a correct position with respect to the arms 120, 122 to conduct bipolar energy to the tips 220a, 220b. Alternatively, points 202a, 202b may be pads formed as concave dimples or generally flat surfaces designed to mate with points 204a, 204b that are conductive pogo sticks, or vice versa. In one example, points 202a, 202b, and points 204a, 204b may cooperate to both provide a conductive path and yieldably lock the end effector 80 in place with respect to the arms 120, 122 in the first position.

Still further, one of points 202a, 202b, points 204a, 204b, or both sets of points can include mating conductive surfaces that are hidden from view until the device is configured in the first position. As such, one or both sets of points 202a, 202b and points 204a, 204b are insulated from contact when not in use.

In FIG. 10, the device 30 is configured such that the end effector second, monopolar end 84 projects distally from the arms 120, 122 while the end effector first, bipolar end 82, partially obstructed from view by arm 120, is received in gap or spacing 150 as described above. In this configuration, a monopolar electrode blade 230 projects from a now-distal face 386 of end effector body 81. The monopolar electrode blade 230 includes a blade tip 232 which may be formed by opposed, concave side walls 234a, 234b and may taper such as shown to form a sharp or razor-like blade member 23.

Electrode blade 230 configured to be electrically coupled to a source of bipolar RF energy supplied from an electrosurgical unit, such as electrosurgical unit 10. Device 30 further includes monopolar contact points 240 disposed on a clevis arm, such as on arm 122. Contact point 240 is configured to mate with contact points 242 disposed on end effector 80, when the device is configured in the second position to operate in monopolar mode. When contact point 240 mates with contact point 242 on the end effector 80, the device 30 is configured to transfer electrical energy from the switch on the handpiece 100, such as pushbutton 114, to the electrode blade 230. In one example, RF energy from an electrical surgical unit can be transferred through mated points 240 and 242 to electrode blade 230. In another example, mated points 240, 242 can be used to complete a connection between another conductor used to transfer RF energy from the electrosurgical unit and the electrode blade 230.

Figure 11:
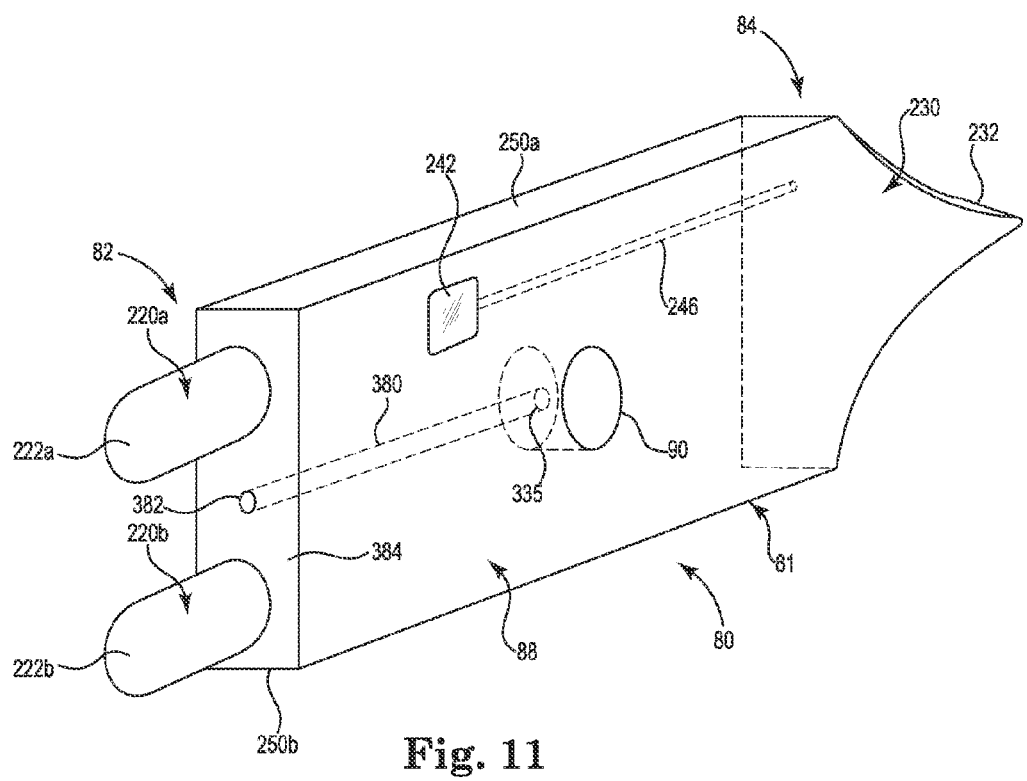
FIG. 11 is another close-up perspective view of the end effector of the electrosurgical device of FIG. 5 showing inner structures in phantom.

FIG. 11 illustrates another perspective view of end effector 80 with inner structures shown in phantom. Electrode blade 230 includes an electrically conductive material such as metal and may comprise stainless steel, titanium, gold, silver, platinum or any other suitable material. The electrode blade 230 is electrically coupled to a conductive monopolar electrode path 246 that may comprise an electrically conductive material and may be configured as a wire or wire trace, or other conductor, disposed within the end effector body 81. In some examples, path 246 may be covered with an insulator material if disposed on the surface of the end effector body 81. Conductive monopolar electrode path 246 extends from electrode blade 230 to monopolar electrode point 242. Monopolar electrode point 242 is provided on the second side or surface 88 of end effector 80. The point 242 is configured to frictionally contact a mating monopolar electrode point 240 provided on a surface of an arm, such as the second arm 122 in the example, of the device 30.

In one example, points 240 and 242 are electrically conductive pads. When the conductive monopolar electrode point 242 makes friction contact with mating monopolar point 240 on arm 120, monopolar energy may be delivered from an electrosurgical unit 10 via depression of push button 114. Energy from the unit 10 may be delivered via electrically conductive, insulated shafts within the handle 101 and arm 122. An electrically conductive path may thus be established from a proximal end 104 of handle 101, through second arm 122 and to mating electrode points 240, 242. In this manner, monopolar electrical energy may be delivered to tissue via monopolar electrode blade 230. When the device 30 is configured as shown in FIG. 9, the device 30 may be considered to be in a monopolar or cutting mode.

Point 240 and point 242 may take other suitable forms. For example, point 240 may be a pad formed as a concave dimple or as a generally flat surface designed to mate with point 242 that is a pad formed as concave bumps, or vice versa. The dimple and bump design may also provide a tactile sensation indicating the end effector 80 is in a correct position with respect to the arms 120, 122 to conduct monopolar energy to the electrode blade 230. Alternatively, point 240 may be a pad formed as a concave dimple or generally flat surface designed to mate with point 242 that is a conductive pogo stick, or vice versa. In one example, point 240 may cooperate with point 242 to both provide a conductive path and yieldably lock the end effector 80 in place with respect to the arms 120, 122 in the second position.

Still further, point 240, point 242, or both points 240, 242 can include mating conductive surfaces that are hidden from view until the device is configured in the second position. As such, one or both points 240, 242 can be insulated from contact when not in use.

The examples show points disposed proximate the lateral edges of both the arms 120, 122 and end effector 80 for illustration only. Points 202a, 202b and point 240 can be placed anywhere on arms 120, 122 such as on the lateral edges or inner surfaces 124, 126. Points 204a, 204b and point 242 can be placed anywhere on end effector 80 such as on end effector sides 86, 88 or end effector lateral edges 250a, 250b.

As described above, multipurpose electrosurgical device 30 comprises a novel wiring concept which allows for selective adjustment of a rotatable end effector 80 comprising opposed bipolar and monopolar electrode ends 82, 84. While in a bipolar sealing or electrocautery mode, bipolar energy is supplied to the rotating end effector bipolar end via electrically conductive bipolar mating points 204a, 204b and 202a, 202b and selectively applied via pushbutton 116. In one example, bipolar energy is provided from the electrosurgical unit 10 to the electrode tips 220a, 220b in the range of 70 to 200 watts for coagulation or sealing. While in monopolar or cut mode, the device 30 again makes friction contact and monopolar energy is supplied to the rotating end effector monopolar end 84 via electrically conductive monopolar mating points 240, 242 and selectively applied via pushbutton 114. In one example, monopolar energy is provided from the electrosurgical unit 10 to the electrode blade 230 in the range of 10 to 50 watts for cutting.

As described above, the use of the electrically conductive points on rotatable end effector 80 that mate with electrically conductive points on the arms 120, 122 uniquely allows a desired working electrode end to be selectively changed from coagulation or sealing (bipolar) mode to a cutting (monopolar) mode and to allow the end effector 80 to rotate freely with respect to the arms 120, 122 without twisting wires or otherwise straining conductors.

Figure 12:
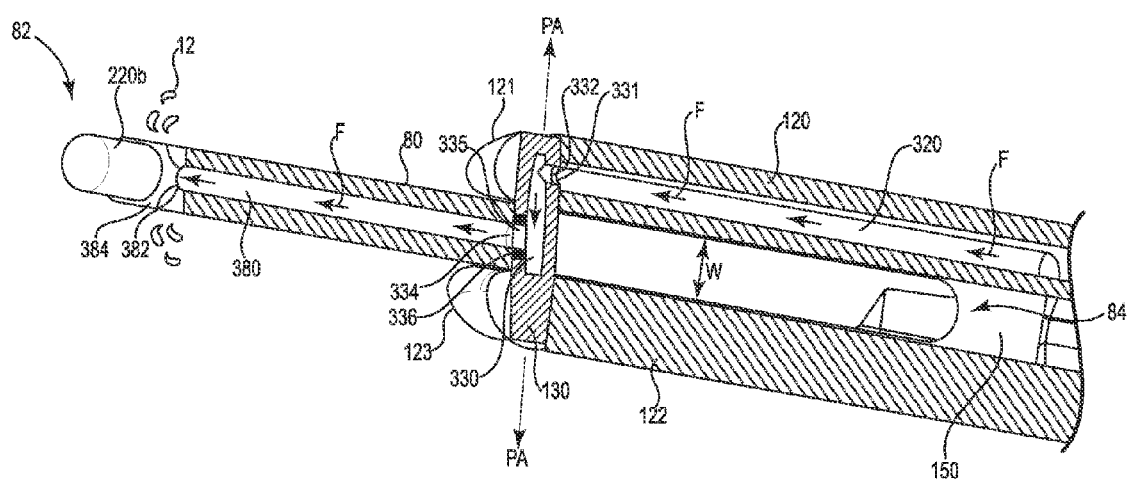
FIG. 12 is a close-up cross-sectional view of a distal end of an electrosurgical device configured in FIG. 8 for use in the bipolar mode.
Figure 13:
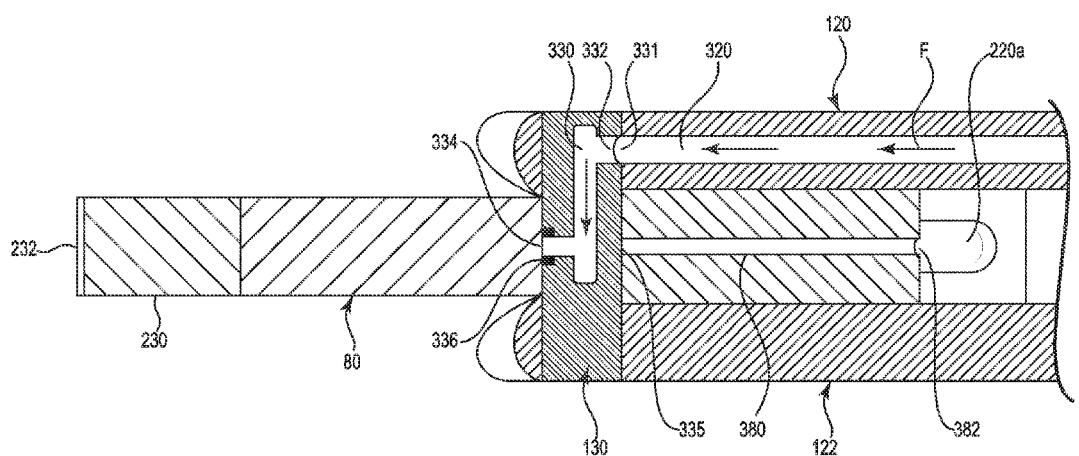
FIG. 13 is a close-up cross-sectional view of a distal end of an electrosurgical device configured in FIG. 10 for use in the monopolar mode.

When the device 30 is configured for use in a bipolar mode, fluid 12 may be delivered to tissue concurrently with the delivery of electrical energy. FIGS. 12 and 13 illustrate example details of the fluid delivery structures. FIGS. 9 and 11 illustrate the end effector 80 decoupled from the clevis pin 80 and handpiece 100 and show portions of the fluid delivery structure of the end effector 80 in phantom. The device 30 is configured to receive fluid 12 from tubing 16 at the proximal end 104 and deliver it to the end effector 80 while in the first position.

FIG. 12 is a cross-sectional view of a distal end of device 30 in the first position and shows an embodiment of a fluid flow pathway indicated by arrows F extending from a proximal end 104 to an opening 382 on the face 384 of the bipolar end 82 of end effector 80. In one example, the pathway F comprises at least three fluid delivery lumens including arm lumen 320, pin lumen 330, and end effector lumen 380. Fluid 12 may be communicated from a source 20, through one or more fluid passages within handle 101 to arm lumen 320. At least one arm, such as the first arm 120, comprises an arm lumen 320 capable of being fluidly coupled to a pin lumen 330 formed in clevis pin 130. Arm 120 includes an arm outlet 331 and clevis pin 130 includes at least one sealed fluid inlet 332 for receiving fluid into lumen 330. Clevis pin 130 further includes at least one sealed fluid outlet 334 for fluidly coupling lumen 330 to end effector inlet 335 into end effector lumen 380 of end effector body 81. Fluid 12 may exit the end effector body 81 at an end effector outlet 382 provided on a face 384 of the end effector first end 82.

The clevis pin 80 can include a seal member such as ring 336 as part of clevis outlet 334, such as a low durometer polyvinyl chloride ring, to act as a seal in the junction of the clevis lumen 330 and end effector lumen 380, which move relative to one another in the example as the end effector 80 is rotated with respect to the arms 120, 122. Alternatively, the seal member can be disposed at the end effector inlet 335.

FIG. 13 is a cross-sectional view of the distal end of the device 30 in the second position and shows a configuration where the fluid low path indicated by arrows F is cut off from reaching the outlet 382 on the end effector 80. The presence of fluid 12 near the electrode blade 340 can impede the ability use the device in a cutting mode. In the example shown, the end effector 80 rotates about axis PA with respect to the arms 120, 122 and clevis pin 130. The clevis pin 130 acts as a ball valve to cut off fluid communication to the end effector lumen 380. For instance, clevis outlet 334 is not aligned with end effector inlet 335 so fluid is not communicated between clevis pin lumen 330 and end effector lumen 380. In this manner, fluid 12 is stopped from entering into the end effector 80 while the end effector is in the second position for monopolar mode as well as while the end effector 80 is in partial rotation. Ring 336 inhibits fluid from leaking from the clevis lumen 330.

In another example, the clevis pin 130 can be coupled to the end effector 80 such that the clevis pin rotates with the end effector 80 about axis PA with respect to the arms 120, 122. In this example, the clevis pin acts as a ball valve at to cut off fluid communication into the clevis pin lumen 330 and end effector lumen 380. For instance, arm outlet 331 is not aligned with clevis pin inlet 332 while the end effector 80 is in the second position or in partial rotation if the clevis pin is rotated with the end effector 80 with respect to the arms 120, 122. In this example, a seal member, such as a ring, can be included at the arm outlet 331 (or on clevis inlet 332) to inhibit fluid from leaking from arm lumen 320.

As described above, the use of the fluid delivery lumen on rotatable end effector 80 that mate with lumens on the arms 120, 122 and clevis pin 130 uniquely allows a desired working electrode end to be selectively changed from coagulation or sealing (bipolar) mode to a cutting (monopolar) mode and to allow the end effector 80 to rotate freely with respect to the arms 120, 122 without kinking or otherwise straining a fluid delivery tubing.

FIG. 11 illustrates end effector outlet 382 on face 384 of end effector first end 82 to disperse fluid 12 while in bipolar mode. End effector outlet 382 in the example is located between electrode tips 220a, 220b. Other configurations are possible, such as the lumen within the end effector may branch and fluid can be dispersed from multiple openings located on the face 384 and or lateral sides 250a, 250b of the end effector 80.

Although the present disclosure has been described with reference to preferred embodiments, workers skilled in the art will recognize that changes can be made in form and detail without departing from the spirit and scope of the present disclosure.

What is claimed is:

1. A multipurpose electrosurgical device comprising:
   a handle;
   a first arm and a second arm extending distally from the handle, the first and second arms laterally spaced from one another to provide a gap between the first and second arms;
   an end effector rotatably coupled to the first and second arms;
   wherein the end effector comprises bipolar and monopolar electrode ends; and
   wherein the end effector is configured to rotate such that the bipolar and monopolar electrode ends are rotatable with respect to the first and second arms to selectively configure the device in a bipolar mode and a monopolar mode.

2. The multipurpose electrosurgical device of claim 1, wherein when the device is configured in a monopolar mode, at least a portion of the bipolar electrode end is received in the gap and the monopolar electrode end extends distally from the first and second arms and when the device is in a bipolar mode, at least a portion of the monopolar electrode end is received in the gap and the bipolar electrode end extends distally from the first and second arms.

3. The multipurpose electrosurgical device of claim 1, wherein the bipolar electrode end comprises first and second laterally spaced bipolar electrode tips and the monopolar electrode end comprises a monopolar electrode blade.

4. The multipurpose electrosurgical device of claim 3, wherein the end effector comprises first and second bipolar electrode paths coupled to and extending from the first and second electrode tips to first and second bipolar electrode points, wherein the first and second bipolar electrode points are configured to electrically couple to first and second mating bipolar points, respectively, provided on a surface of the first arm; and
   wherein the end effector further comprises a monopolar electrode path coupled to and extending from the electrode blade to a monopolar electrode point, wherein the monopolar electrode point is configured to electrically couple to a mating monopolar point provided on a surface of the second arm.

5. The multipurpose electrosurgical device of claim 4 wherein the first and second bipolar electrode points and the first and second mating bipolar points are a first set of conductive pads, and the first and second electrode points are configured to frictionally contact the first and second mating bipolar points, respectively; and wherein the monopolar electrode point and the mating monopolar point are a second set of conductive pads, and the monopolar electrode point is configured to frictionally contact the mating monopolar point.

6. The multipurpose electrosurgical device of claim 4 wherein one of the first and second bipolar electrode points and the first and second mating bipolar points are dimpled electrical pads and the other of the first and second bipolar electrode points and the first and second mating bipolar points are electrical pad bumps.

7. The multipurpose electrosurgical device of claim 4, wherein when the first and second bipolar electrode points are coupled to the first and second mating bipolar points, respectively, bipolar energy may be delivered to the first and second bipolar electrode tips from an electrosurgical unit.

8. The multipurpose electrosurgical device of claim 4, wherein the first and second bipolar electrode paths and the monopolar electrode path comprise electrically conductive wires disposed within the end effector.

9. The multipurpose electrosurgical device of claim 1, wherein the first arm comprises a first arm fluid lumen, and the end effector comprises an end effector fluid lumen, wherein the first arm fluid lumen and the end effector fluid lumen are configured to be in fluid communication while in bipolar mode.

10. The multipurpose electrosurgical device of claim 9, wherein the first arm fluid lumen and the end effector fluid lumen are configured to not be in fluid communication while in the monopolar mode.

11. The multipurpose electrosurgical device of claim 9, wherein the end effector is coupled to the first and second arms via a pin comprising a sealed fluid lumen in fluid communication with the first arm lumen and end effector fluid lumen while in the bipolar mode.

12. The multipurpose electrosurgical device of claim 11, wherein the sealed fluid lumen is configured to be in fluid communication with one of the first arm lumen and the end effector fluid lumen and not the other of the first arm lumen and the end effector lumen while in the monopolar mode.

13. A multipurpose electrosurgical device comprising:
a handpiece having a handpiece proximal end and a handpiece distal end extending along a longitudinal axis; and
an end effector having a monopolar electrode and a pair of bipolar electrodes spaced-apart from the monopolar electrode, the end effector coupled to the handpiece and selectively rotatable about a rotational axis perpendicular to the longitudinal axis and relative to the handpiece from a first position to a second position;
wherein the first position includes the bipolar electrodes extending distally from the device along the longitudinal axis and the monopolar electrode is spaced from a distal end portion of the device; and
wherein the second position includes the monopolar electrode extending distally from the device along the longitudinal axis and the bipolar electrodes are spaced from the distal end portion of the device.

14. The multipurpose electrosurgical device of claim 13 wherein the handpiece includes a handle and a plurality of arms extending distally from the handle wherein the end effector is coupled to the arms.

15. The multipurpose electrosurgical device of claim 14 wherein the end effector is rotatably coupled to the arms to rotate about the rotational axis.

16. The multipurpose electrosurgical device of claim 15 wherein the end effector is configured to rotate about the rotational axis in a first direction and in a second direction opposite the first direction.

17. The multipurpose electrosurgical device of claim 13 wherein the handpiece includes a switch mechanism.

18. The multipurpose electrosurgical device of claim 17 wherein the bipolar electrodes are electrically coupled to the switch mechanism in the first position and the monopolar electrode is not electrically coupled to the switch mechanism in the first position.

19. The multipurpose electrosurgical device of claim 17 wherein the monopolar electrode is electrically coupled to the switch mechanism in the second position and the bipolar electrodes are not electrically coupled to the switch mechanism in the second position.

20. The multipurpose electrosurgical device of claim 17 wherein the switch mechanism includes a plurality of push buttons.

21. The multipurpose electrosurgical device of claim 13 wherein the device comprises a fluid delivery pathway extending from a proximal end of the device to an opening on a distal end of the end effector when the device is configured in the first position.

22. The multipurpose electrosurgical device of claim 21 wherein the handpiece includes a handpiece lumen and the end effector includes an end effector lumen in communication with the opening, wherein the fluid delivery pathway includes the handpiece lumen in fluid communication with the end effector lumen when the device is configured in the first position.

23. The multipurpose electrosurgical device of claim 22 wherein the handpiece lumen is not in fluid communication with the opening when the device is configured in the second position.

24. The multipurpose electrosurgical device of claim 21 wherein the fluid delivery pathway is blocked when the device is configured in the second position.

25. The multipurpose electrosurgical device of claim 13 wherein the end effector includes a bipolar end and a monopolar end axially opposed to the bipolar send, wherein the bipolar electrodes are disposed on the bipolar end and the monopolar electrode is disposed on the monopolar end.

26. The multipurpose electrosurgical device of claim 13 wherein the first position includes the monopolar electrode disposed within the handpiece and the second position includes the bipolar electrodes disposed within the handpiece.

27. A method of selectively configuring an electrosurgical device for use in a bipolar and a monopolar mode comprising:
configuring the device in a bipolar mode by rotating an end effector rotatably coupled to first and second arms extending distally from a handle of the device to position a bipolar end of the end effector such that the bipolar end extends distally from the handle and a monopolar end of the end effector is at least partially received within an open space between the first and second arms; and
configuring the device in a monopolar mode by rotating the end effector to position the monopolar end of the end effector such that the monopolar end extends distally from the handle and the bipolar end is at least partially received within the open space;
wherein rotating the end effector comprises rotating the end effector by hand.

28. The method of selectively configuring an electrosurgical device for use in a bipolar and a monopolar mode of claim 27, wherein positioning the bipolar end further comprises mating first and second bipolar electrode pads on the end effector with first and second mating bipolar pads on the first arm and positioning the monopolar end further comprises mating a monopolar electrode pad on the end effector with a mating monopolar pad on the second arm.

* * * * *